United States Patent
Killion

(10) Patent No.: US 10,357,402 B2
(45) Date of Patent: Jul. 23, 2019

(54) METHOD AND SYSTEM FOR DETERMINING THE OCCLUSION EFFECT IN AN EARPIECE

(71) Applicant: Etymotic Research, Inc., Elk Grove Village, IL (US)

(72) Inventor: Mead C. Killion, Elk Grove Village, IL (US)

(73) Assignee: Etymotic Research, Inc., Elk Grove Village, IL (US)

( * ) Notice: Subject to any disclaimer, the term of this patent is extended or adjusted under 35 U.S.C. 154(b) by 24 days.

(21) Appl. No.: 15/230,456

(22) Filed: Aug. 7, 2016

(65) Prior Publication Data
US 2017/0041728 A1 Feb. 9, 2017

Related U.S. Application Data

(60) Provisional application No. 62/202,624, filed on Aug. 7, 2015.

(51) Int. Cl.
| | |
|---|---|
| *H04R 1/10* | (2006.01) |
| *A61F 11/08* | (2006.01) |
| *H04R 25/00* | (2006.01) |

(52) U.S. Cl.
CPC ............ *A61F 11/08* (2013.01); *H04R 1/1016* (2013.01); *H04R 25/652* (2013.01); *H04R 2460/15* (2013.01)

(58) Field of Classification Search
None
See application file for complete search history.

(56) References Cited

U.S. PATENT DOCUMENTS

| | | | | | |
|---|---|---|---|---|---|
| 5,577,511 | A | * | 11/1996 | Killion | A61B 5/121 381/60 |
| 2009/0129619 | A1 | * | 5/2009 | Nordahn | H04R 25/70 381/328 |
| 2011/0299692 | A1 | * | 12/2011 | Rung | H04R 25/70 381/60 |

OTHER PUBLICATIONS

Killion; Mead C., The "Hollow Voice" occlusion effect, Sep. 22, 1988 https://www.etymotic.com/media/publications/erl-0088-1988.pdf.*

* cited by examiner

*Primary Examiner* — Yogeshkumar Patel
(74) *Attorney, Agent, or Firm* — McAndrews, Held & Malloy, Ltd.

(57) ABSTRACT

Provided is a disclosure for measuring the occlusion effect due to the depth of seal of the earpiece in the ear canal using a single microphone.

23 Claims, 9 Drawing Sheets

METHOD AND SYSTEM FOR DETERMINING THE OCCLUSION EFFECT IN AN EARPIECE

RELATED APPLICATION(S)

This application claims the benefit of the U.S. Provisional Application 62/202,624, titled "Method for Estimating Depth of Ear Tip in Ear Canal" and filed on Aug. 7, 2015, the disclosure of which is incorporated herein in its entirety by reference.

BACKGROUND

The present disclosure relates to hearing technology, and more particularly, to a method and system for determining the occlusion effect in an earpiece.

In the fitting of hearing protection devices (HPD), measurements are made of the attenuation provided by the HPD as well as whether there is any occlusion effect due to the actual earpiece of the HPD. Occlusion effect, or additional noise heard by the HPD user due to the user's voice bouncing off the earpiece of the HPD, may be bothersome to the user. Measurement of attenuation is typically done by measuring the sound pressure level (SPL) on the outer side of the ear canal open to the air and comparing it to the SPL measured on the inner side of the ear canal blocked by the HPD.

The occlusion effect is typically measured by comparing SPLs generated by the wearer's voice, for example, within the ear canal without the earpiece with the SPLs generated within the ear canal with the earpiece in place. These sound pressure differences provide an indication of the degree of occlusion provided by the earpiece. The term "degree of occlusion" is used to refer to the degree to which an occluding object, such as an earpiece, prevents leakage and/or inhibits occlusion effect. In most instances, the measured difference between the SPLs described above provide a quantitative measure of the degree of occlusion of an occluding object.

The failure of an earpiece to properly seal and fit within the ear canal of a subject can result in unwanted repercussions. Without a close fit between the earpiece and the ear canal wall, excessive leakage may result. This excessive leakage may result in reducing the effectiveness of the HPD. With respect to occlusion effect, the bone conduction of the wearer's voice may be amplified when the ear is occluded. The HPD wearer's own voice is thus heard as being loud and distorted. This effect was noted by J. Zwislocki in his article entitled "Acoustic Attenuation Between The Ears", J. Acous. Soc. Amer. 25:752-759 (1953). The value of deeply sealed earpieces to eliminate this effect is discussed in an article by Mead Killion entitled "The 'Hollow Voice' Occlusion Effect" Hearing Aid Fitting—Theoretical and Practical Views, CH. III, pp. 231-242 (1988). It is therefore important in some fittings to ensure that the earpiece seal extends far enough into the ear canal to eliminate this occlusion effect.

Further limitations and disadvantages of conventional and traditional approaches to measuring occlusion effect will become apparent to one of skill in the art, through comparison of such systems with some aspects of the present disclosure as set forth in the remainder of the present application with reference to the drawings.

SUMMARY

A method and system for determining the occlusion effect in an earpiece, substantially as shown in and/or described in connection with at least one of the figures, as set forth more completely in the claims.

Various advantages, aspects, and novel features of the present disclosure, as well as details of an illustrated embodiment thereof, will be more fully understood from the following description and drawings.

BRIEF DESCRIPTION OF THE DRAWINGS

These and/or other aspects will become apparent and more readily appreciated from the following description of the exemplary embodiments, taken in conjunction with the accompanying drawings.

DETAILED DESCRIPTION

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

It will also be understood that terms coupled, connected, attached, and the like include both direct and indirect (e.g., with an intervening element) coupling, connecting, attaching, etc., unless explicitly indicated otherwise. For example, if element A is coupled to element B, element A may be indirectly coupled to element B through an intermediate signal distribution structure, element A may be directly coupled to element B (e.g., adhered directly to, soldered directly to, attached by direct metal-to-metal bond, etc.), etc.

Software component may refer to executable code and/or data used by the executable code in an addressable storage medium. Thus, software components may be, for example, object-oriented software components, class components, and task components, and may include processes, functions, attributes, procedures, subroutines, segments of program code, drivers, firmware, micro codes, circuits, data, a database, data structures, tables, arrays, or variables.

Reference will now be made in detail to embodiments, examples of which are illustrated in the accompanying drawings. In this regard, the present embodiments may have different forms and should not be construed as being limited to the descriptions set forth herein.

In the following description, well-known functions or constructions might not be described in detail so as not to obscure the embodiments with unnecessary detail. Additionally, while the device that goes in to the ear canal is termed as "earpiece," other terms such as "earplug" and "earmold" can also be used interchangeably.

Figure 1:
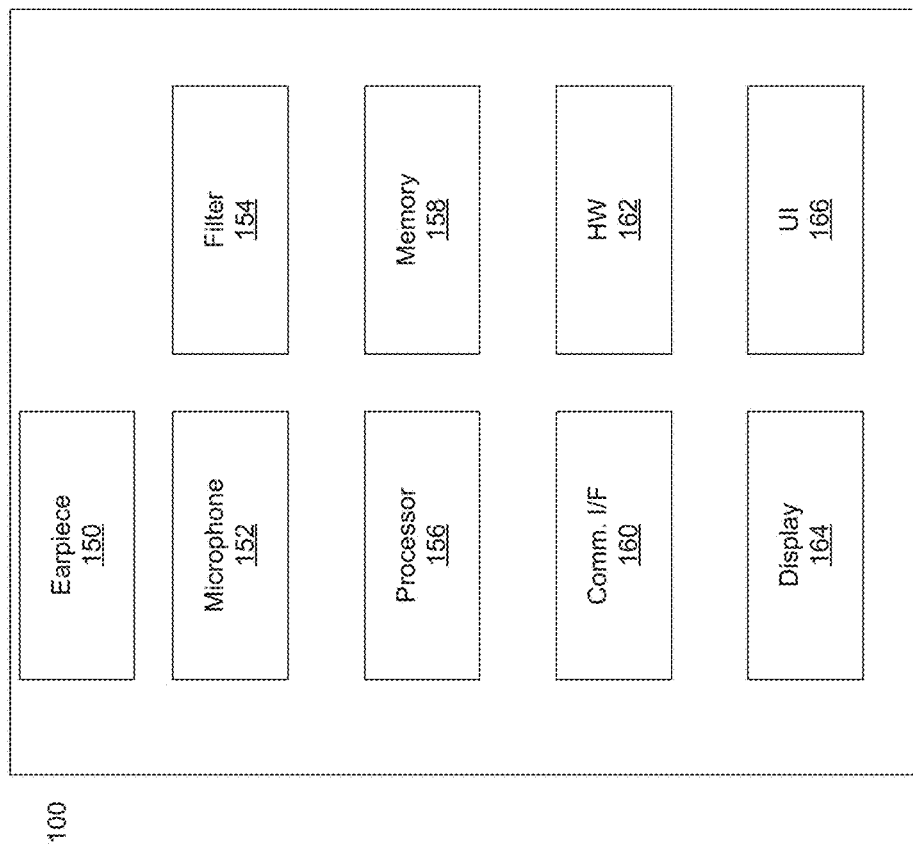
FIG. 1 is an example block diagram for a measurement device in accordance with an embodiment of the disclosure.

FIG. 1 is an example block diagram for a measurement device in accordance with an embodiment of the disclosure. Referring to FIG. 1, there is shown measurement device 100 comprising an earpiece 150, a microphone 152, a filter block 154, a processor 156, memory 158, communications interface 160, hardware block 162, a display 164, and a user interface 166.

The measurement device 100 is shaped to be inserted in to an ear canal. In particular, the earpiece 150 is inserted in to the ear canal. Some embodiments of the measurement device 100 may be entirely in the earpiece 150, while other embodiments may have portions of the measurement device 100 in the earpiece 150. The microphone 152 can be used to receive sound waves from the inner ear and convert them to electrical signals. The sound waves can be detected in some cases by the microphone 152 that is at the inner edge of the measurement device 100. In other cases, the microphone 152 may be in the measurement device 100, in the ear canal exposed to the environment, or even external to the ear. The sound waves may then travel through a probe tube (not shown) to the microphone 152. The probe tube may be a small tube that leads from the portion of the ear canal that is blocked from the environment by the measurement device 100. The probe tube may be outside the earpiece or go through the earpiece. Examples of the probe tube can be seen in FIGS. 4, 5, 7, and 9.

The filter block 154 can be used to filter the signals from the microphone 152 to generate a filtered output. As will be explained later, the frequency of interest is in the region of approximately 250 Hz. Accordingly, the filter block 154 may be a low pass filter that passes signals at or below, for example, a cutoff frequency of 500 Hz. While a cutoff frequency of 500 Hz was chosen as an example, various embodiments need not have this exact cutoff frequency. For example, the cutoff frequency may be 400 Hz. The specific filter characteristics are dependent on design considerations.

The filter block 154 may also be a bandpass filter that passes the frequencies of interest, such as, for example, frequencies around a center frequency of 250 Hz and a passband of 300 Hz. Again, the example center frequency and pass band given need not limit any specific embodiment of the disclosure. The specific filter characteristics are dependent on design considerations.

The filter block 154 may perform any type of appropriate filtering, whether digital or analog, or even by digital signal processing. A filter block 154 may be, for example, part of the measurement device 100 that is outside the ear canal. This may be, for example, because it is deemed to be too large to fit in an ear canal or if it is deemed to generate too much heat. If the filter block 154 performs filtering via digital signal processing, the filter block 154 can be, for example, a digital signal processor (DSP). In some cases, the filtering may be performed by a processor such as the processor 156 that runs a software filtering program. The digital signal processing and/or software filtering may require the analog signals from the microphone 152 to be converted to digital signals via, for example, sampling. The sampling circuits may be part of the filter block 154 or the hardware block 162. Accordingly, some embodiments may have some portion of the processing performed digitally.

Figure 7:
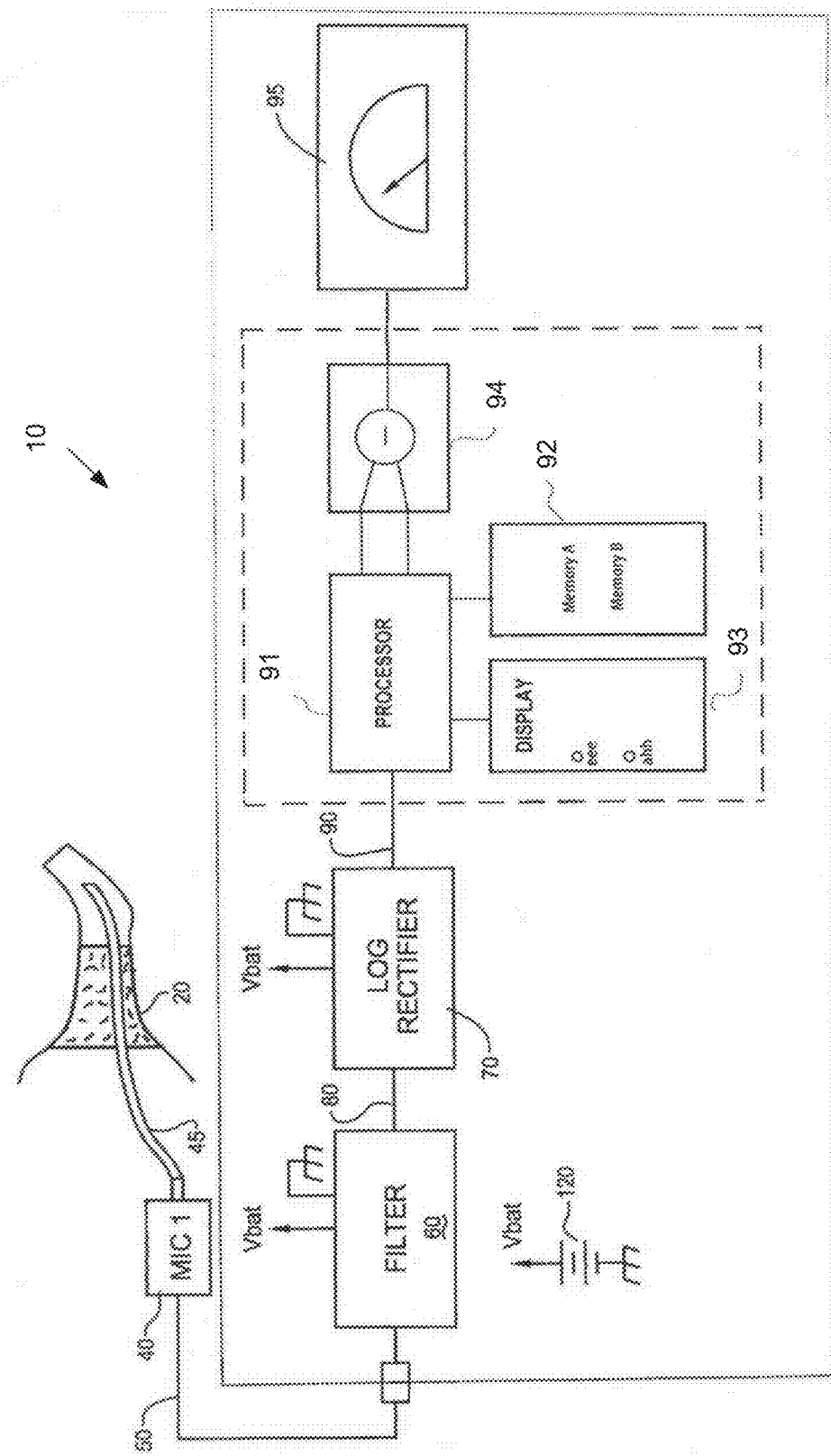
FIG. 7 is an example circuit diagram illustrating operation of an SPL measuring device, in accordance with an embodiment of the disclosure.

The filter block 154 may also comprise a rectifier unit, which may include an amplifier unit (shown in FIG. 7). The rectifier unit can be used to obtain DC signals from AC signals. The amplifier may be used to boost the strength of signals so that they can be processed appropriately.

The processor 156 may be a central processing unit, a controller, an ASIC, etc. that can execute instructions to perform various tasks. One such task may be, for example, performing software filtering of the electrical signals from the microphone 152 after they have been converted to digital signals. The processor 156 may also be used to control the operation of the measurement device 100 in general.

The memory 158 can comprise volatile and non-volatile memory, where data and executable code can be stored. The data stored may be, for example, the electrical signals from the microphone 152 that have been processed (filtered, rectified, amplified, sampled, etc.) to a digital form. The various signals from the microphone 152 may be saved in order to have multiple samples from which to determine the occlusion effect, and from the occlusion effect have a good estimate of attenuation.

The communication interface 160 may comprise appropriate circuitry and/or software to support transmitting information to and receiving information from external devices. The communication may be via wired and/or wireless protocols. Some protocols may be, for example, USB, WiFi/WiFi Direct, near field communication, Bluetooth, and various cellular protocols, among others. The communication interface 160 may be used to transmit, for example, display signals to an external display to show the occlusion effect. Similarly, various commands may be received via the communication interface to control the measurement device 100—turn it on, turn it off, start testing, stop testing, etc. Various embodiments may also display the attenuation that can be estimated once the occlusion effect is determined.

Some embodiments may allow the communication interface 160 to transmit the signals from the microphone to be processed, using analog and/or digital circuits, including software as needed, so as to be able to display the occlusion effect on the display 164. Various embodiments may also display the attenuation that may be estimated from the occlusion effect.

While not shown, some embodiments may comprise a speaker so that commands may be given to the user by the measurement device 100, or via the display 164. For example, a prompt may be given to the user to say "AHH" or "EEE."

The hardware block 162 may comprise various hardware that may be needed by the measurement device 100, such as, for example, filters, DSP, analog-to-digital circuit (ADC), and other functions that may be needed to be performed by hardware.

The display 164 may be, for example, an LCD or LED screen that allows display of the occlusion effect. The display 164 may also show, for example, the attenuation that may be estimated from the occlusion effect. The display 164 will be outside the ear canal so the user (or another person) can view the results. The display 164 may receive the display information via wired or wireless communication using, for example, the communication interface 160. The display may also be presented, for example, on an external device such as a smartwatch, a smartphone, a laptop, a PC, a dedicated display, etc. in place of or in addition to the display 164. Some embodiments may allow a prompt to the user to be shown on the display 164.

The user interface 166 may comprise various means for input such as, for example, buttons, knobs, and touch sensitive panel that may be part of the display 164. Input data/commands may also be made via the communication interface, for example.

While various modules of the measurement device 100 have been described, various embodiments may have different configurations that do not use the modules presented. Different embodiments may group the modules 152-166 differently, remove some modules, or add other modules. The presently described modules 152-166 are examples only, and do not limit the embodiments of the disclosure in any way in receiving sound waves and processing them to provide occlusion effect.

A measurement device 100 may be miniaturized for size for portability, and may comprise the display 164. However, various embodiments of the measurement device 100 may also use other display devices such as, for example, a smartwatch, a smartphone, a laptop, a PC, etc. to display occlusion effect (and estimated attenuation in some cases) in place of or in addition to the dedicated display.

Figure 2:
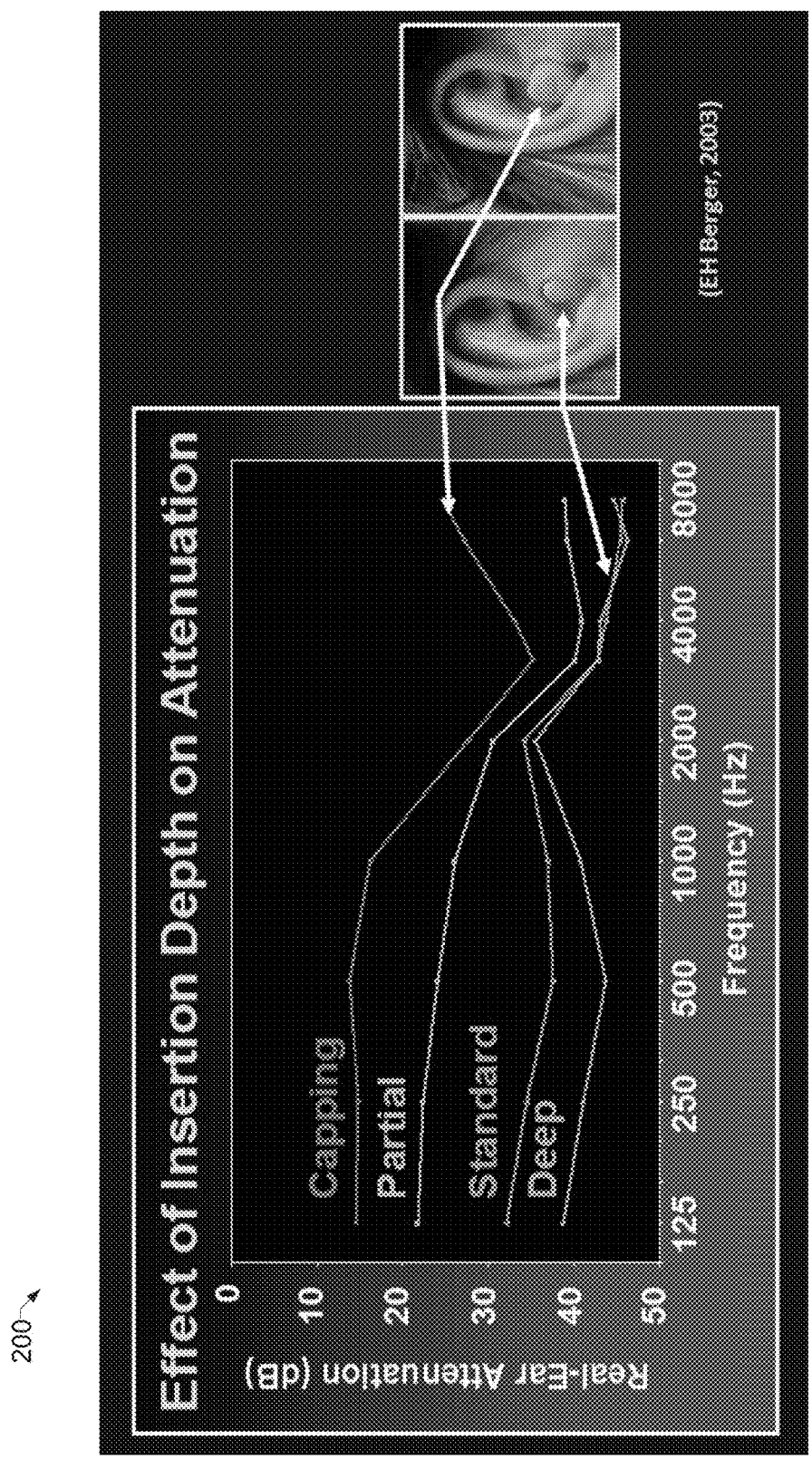
FIG. 2 is graph illustrating examples of attenuation effect based on insertion depth of the HPD.

FIG. 2 is graph illustrating examples of attenuation based on insertion depth of the HPD. Referring to FIG. 2, there is shown a graph 200 with various outputs for attenuation as the insertion depth of a HPD increases. The attenuation of hearing protection devices (HPDs) increases as the location of the seal of the eartip of the device in the ear canal goes from shallow (near the ear canal entrance) to deep. There are four curves shown for four depths, the depths being generally described as "capping" (shallow), "partial," "standard," and "deep." The top curve is for "capping" where the HPD is shallowly inserted in to the ear canal. The second curve from the top is for "partial," the third curve from the top is for "standard," and the bottom curve is for "deep." As can be seen, the depth of insertion of the seal of the eartip of a HPD has appreciable effect in noise attenuation.

Figure 3:
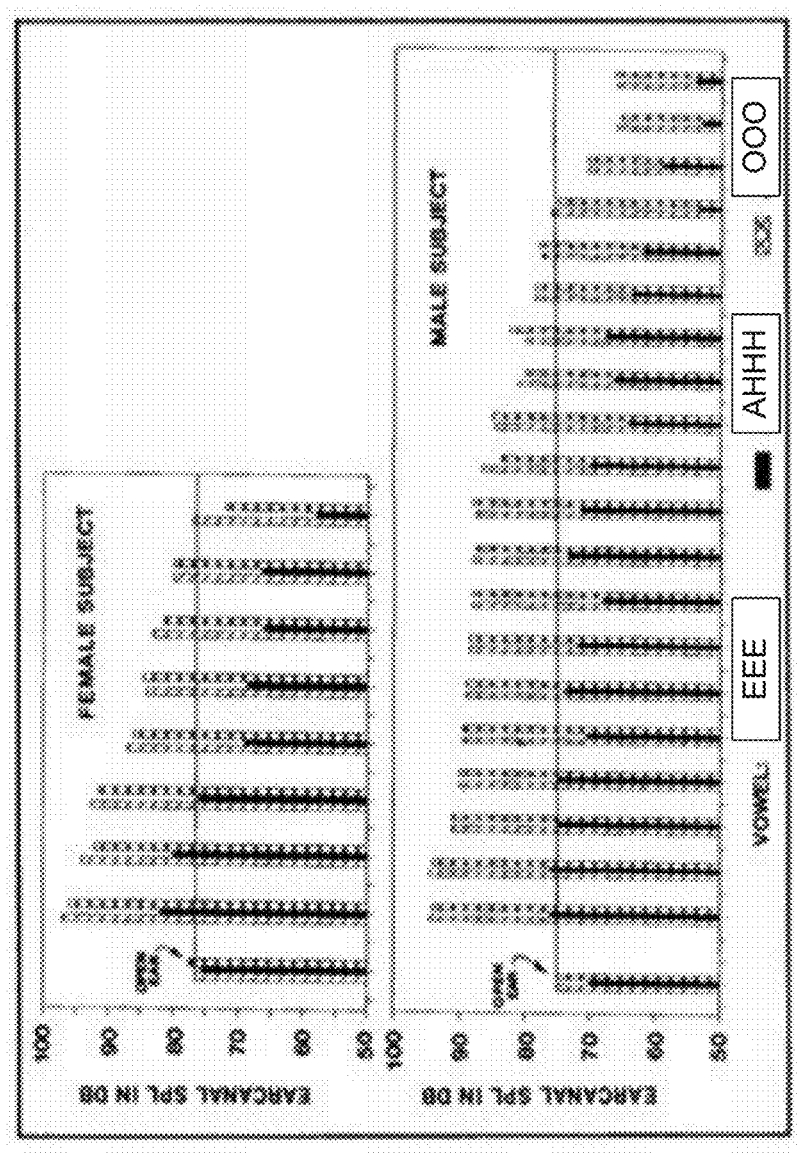
FIG. 3 is a graph illustrating examples of occlusion effect based on insertion depth of the HPD.

FIG. 3 is a graph illustrating examples of occlusion effect based on insertion depth of the HPD. Referring to FIG. 3, there are shown 2 graphs for occlusion effect for women and for men as the insertion depth for an HPD increases along the X-axis. For both men and women, it can be seen that the occlusion effect decreases as the insertion depth increases.

The explanation for both the attenuation and the occlusion effect shown above is because the portion of the ear canal from the entrance to roughly half way to the eardrum is surrounded by relatively soft cartilaginous tissue, which provides relatively low impedance to the motion of the earpiece induced by the sound pressure at the ear, just as the sound of a passing jet can induce enough motion in a window to cause it to rattle. In contrast, the deeper half of the ear canal is surrounded by bone, the hardest bone in the body, which severely limits the motion of an earpiece that is deeply sealed in the ear.

Figure 4:
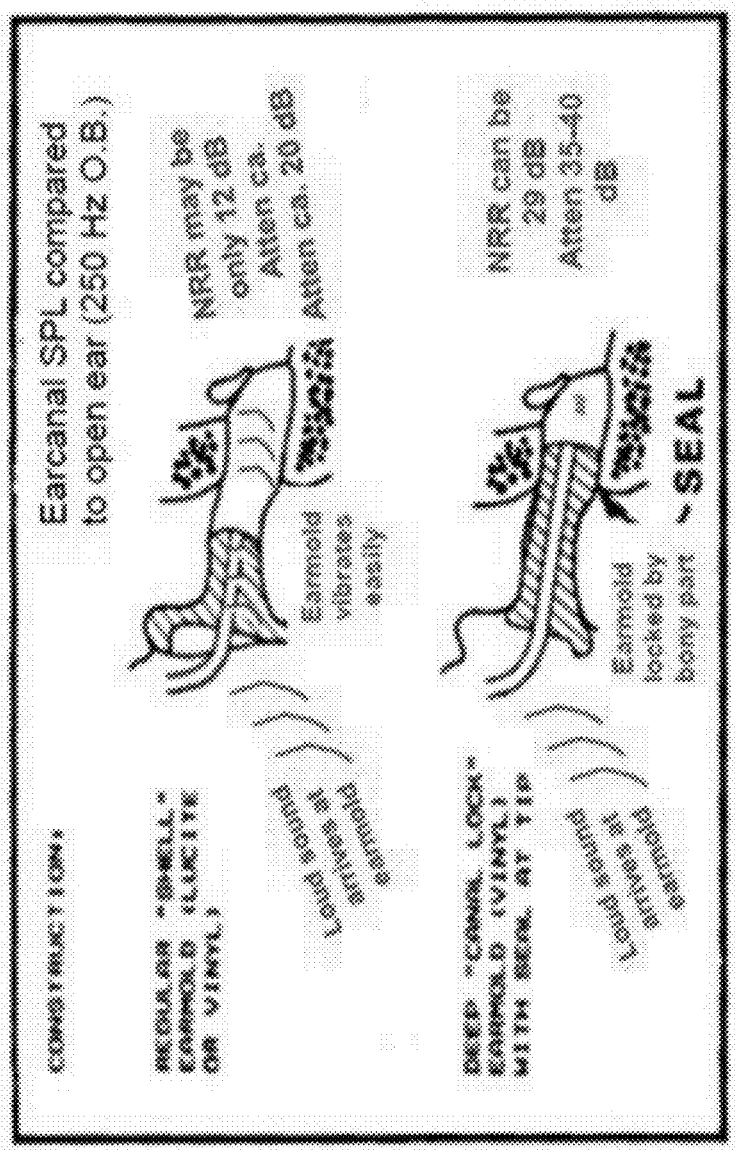
FIG. 4 shows drawings illustrating effect of insertion depths of HPD on attenuation.

FIG. 4 shows drawings illustrating effect of insertion depths of HPD on attenuation. Referring to FIG. 4, there are drawings showing insertion of HPDs in to an ear canal. The upper drawing shows an earpiece of the HPD that is surrounded by the soft cartilage tissue. Accordingly, the attenuation of exterior noise is only 20 dB at 250 Hz. When a HPD is inserted more deeply in to the ear canal so that it is surrounded by the hard bone as shown in the lower drawing, the attenuation of exterior noise is 35-40 dB at 250 Hz.

Figure 5:
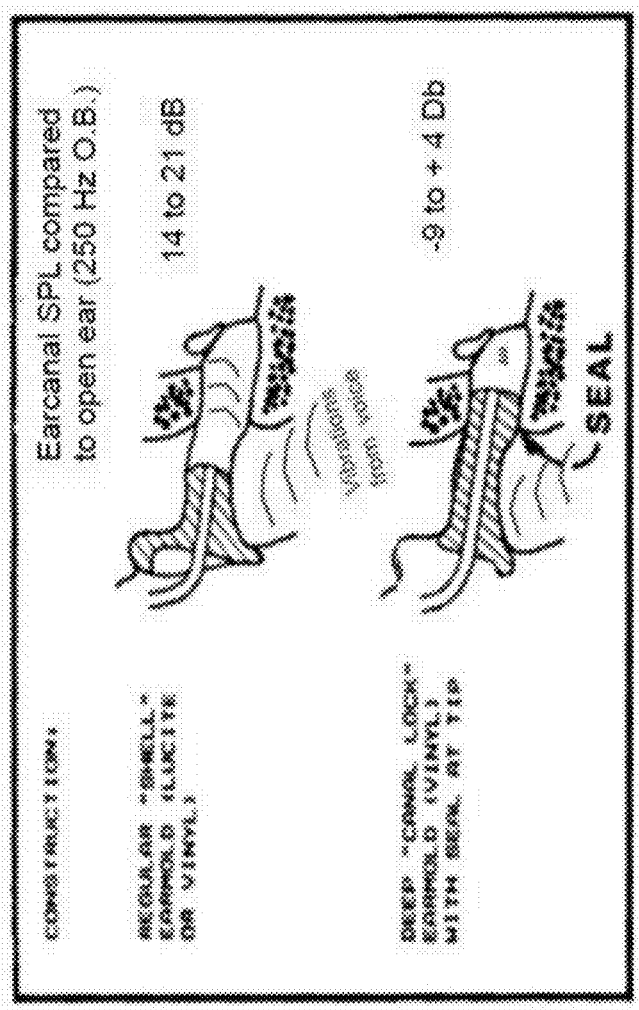
FIG. 5 shows drawings illustrating the effect of insertion depth of the HPD on occlusion effect.

FIG. 5 shows drawings illustrating the effect of insertion depth of HPD on the occlusion effect. Referring to FIG. 5, there are shown drawings showing insertion of HPDs in to an ear canal. Similar to the attenuation drawings of FIG. 4, the upper drawing shown an earpiece of the HPD that is surrounded by the soft cartilage tissue. Accordingly, the occlusion effect is 14-21 dB at 250 Hz. When a HPD is inserted more deeply in to the ear canal so that it is surrounded by the hard bone as shown in the lower drawing, the occlusion effect is −9 to +4 dB at 250 Hz.

The explanation for the difference in occlusion effect between a deeply sealed and shallowly sealed eartip is similar to that of attenuation, but the source of sound—and flesh vibration—is the talker's own voice.

A deeply sealed earpiece can also dramatically reduce the occlusion effect when the wearer speaks. The SPL measured with a probe microphone in the back of the writer's mouth can reach 135 dB SPL on the "closed" vowel "EEE," but only 116 dB SPL on an "open" vowel "AHH" because the open mouth lets the sound spill out. The vibration of the flesh produces the equivalent of a loudspeaker in the cartilaginous portion of the ear canal. The resulting sound normally spills out of the open ear and is not noticed, but a shallow seal allows nearly the entire cartilaginous part of the ear canal to send sound in to the closed volume. The result is much greater SPL in the closed ear with a shallow eartip than with the open ear at low frequencies. These relationships are illustrated in FIG. 5.

It may be pointed out that the SPL at the entrance of the talker's mouth at maximum vocal effort can reach 128 dB on the vowel EEE, and 140 dB on the vowel sound "AHH" because the closed vowel traps the sound inside, while the open vowel lets more of the sound out. An SPL of 140 dB can cause damage in a very short time. Indeed, by NIOSH98 criteria, the so called 85 trade 3 limits, 140 dBA is not safe for even a fraction of a second, yet can be produced by a person yelling directly into someone's ear.

Figure 6:
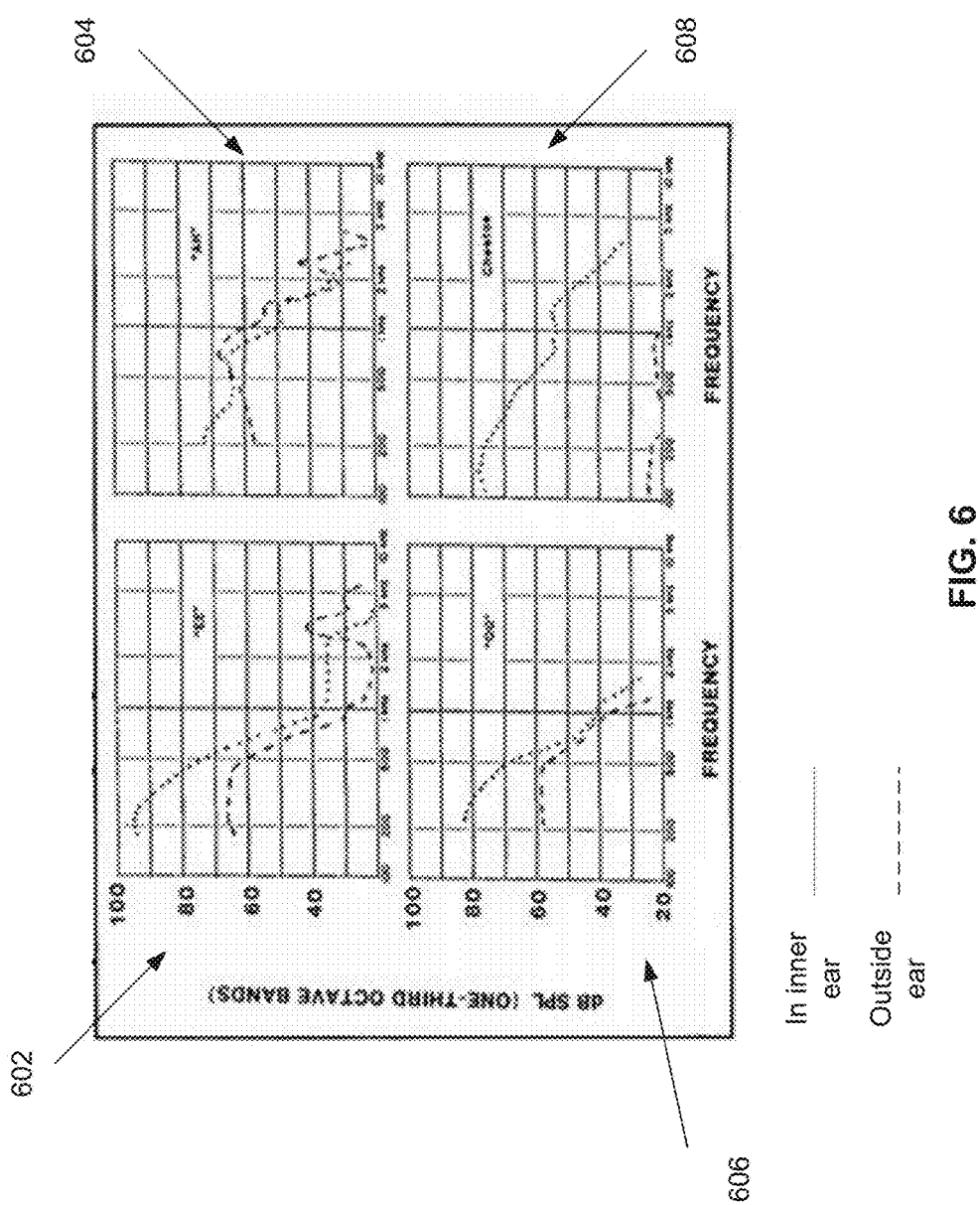
FIG. 6 shows graphs illustrating relationship of SPL measured at different points that can be used with an embodiment of the disclosure.

FIG. 6 shows graphs illustrating relationship of SPL measured at different points that can be used with an embodiment of the disclosure. Referring to FIG. 6, there are shown 4 graphs 602, 604, 606, and 608 that illustrate occlusion effect for different sounds spoken by the same person. Graph 602 is for the sound "EEE," graph 604 is for the sound "AHH," graph 606 is for the sound "OOH," and graph 608 is for the sound made when chewing corn chips. As can be seen in the graphs, the maximum SPL is around the region of 250 Hz.

Various embodiments of the disclosure may use a single objective measurement in the 250 Hz band in the ear canal, for example, of the degree of occlusion effect for a subject's "EEE" vowel sound. As can be seen in FIG. 6, the single objective measurement may provide a good estimate of both the occlusion effect and the attenuation of a hearing protector given the relationship of FIG. 2 between depth of seal and attenuation.

Furthermore, since the vowel sound "AHH" typically produces negligible occlusion effect (little difference between the SPL at the portion of the inner ear blocked from the environment by an earpiece and the SPL at the portion of the inner ear exposed to the environment), the difference in degree of occlusion effect can be readily estimated from the difference between the SPL for the vowel sound "EEE" and the SPL for the vowel sound "AHH." This estimation of the occlusion effect can be made using a single microphone configured to receive sound from the portion of the ear canal blocked from the outside environment by the earpiece.

It will be readily understood that various processing of the electrical signals can be done with analog and/or digital circuits. In some embodiments, various signal processing may be performed by, for example, a DSP, or a processor. One such signal processing may be, for example, bandpass filtering or low pass filtering.

FIG. 7 is an example circuit diagram illustrating operation of an SPL measuring device, in accordance with an embodiment of the disclosure. Referring to FIG. 7, there are shown an earpiece 20, a microphone 40, a probe tube 45, a filter 60, log rectifier 70, and a meter 95. Also shown are a processor 91, memory 92, display 93, and a subtraction module 94. Power may be supplied by battery 120 or equivalent source of voltage and available current as required.

In a brief explanation of the measurement device 10, the microphone 40 receives sound waves for a spoken vowel, for example, via the probe tube 45. The electrical signal 50 from the microphone 40 is received by the filter 60, which processes the electrical signal 50 to a filtered signal 80. The filter 60 may be, for example, a bandpass filter to pass frequencies around 250 Hz.

The filtered signal 80 is processed by the log rectifier 70 to provide a logarithmic DC signal 90. The logarithmic DC signal 90 is then fed to processor 91 then stored in memory 92. A prompt, which may be provided on the display 93, cues the person being tested to utter an "EEE" or "AHH," for example, as appropriate to provide the processor 91 with samples of the two sounds. The processor 91 may then determine the values of the sounds received. The logarithmic DC signal 90 may be analog values that the processor 91 converts to a digital value. Other embodiments may have the log rectifier 70 provide digital values to the processor 91. Still other embodiments may have the filter 60 and the log rectifier 70 be, for example, one module that converts the received electrical signal 50 to digital values and perform digital processing to transmit digital values to the processor 91. Still other embodiments may have the microphone 40 transmit, either wirelessly or via wire, digital signals to the module that may comprise the filter 60 and the log rectifier 70.

Various embodiments may request two or more samples of each sound, and the two sounds may be alternated or not, depending on the embodiment. The values of the sounds may be stored in the appropriate parts of the memory 92 such as, for example, memory A or memory B. The storing of the sounds in the memory 92 may be in fixed locations or variable locations. The difference between the values stored in memories A and B is calculated in the subtraction module 94, and the difference can be displayed, for example, on the meter 95.

The measurement device 10 may use analog circuitry, digital circuitry, or a combination of both, including applicable software. Various embodiments of the disclosure may have the probe tube 45 go alongside the earpiece 20 or through the earpiece 20. As described previously, a microphone such as, for example, the microphone 940 in FIG. 9, may be used to sense the pressure in the ear canal. An example of such a microphone is described in detail in U.S. Pat. No. 9,198,800, issued Dec. 1, 2015. The primary purpose of such a microphone may be that of sensing the soldier's voice for communication. The availability of such a microphone also simplifies the measurements described here since no probe tube is required. As such, the audiologist can utilize the communication device 900 that can be connected to, for example, the measurement device 950 to train the soldiers or other users to routinely obtain a the deep seal of their communications module, assuring maximum hearing protection. The measurement device 950 may be hand-held and/or may contain at least some of the elements of the measurement device 10 of FIG. 7. The measurement device 950 may be able to prompt the user to utter sounds at appropriate times, and display measurement results of the occlusion effect.

A probe tube outside the earpiece 20 may be, for example, moon-shaped and 0.4 mm thick. However, various embodiments of the disclosure need not be limited so. Various designs of probe tubes may be used as appropriate whether the probe tube is inside the earpiece 20 or outside the earpiece 20. An external probe tube may be more versatile since it can be used with many types of HPDs or hearing aids.

Figure 8:
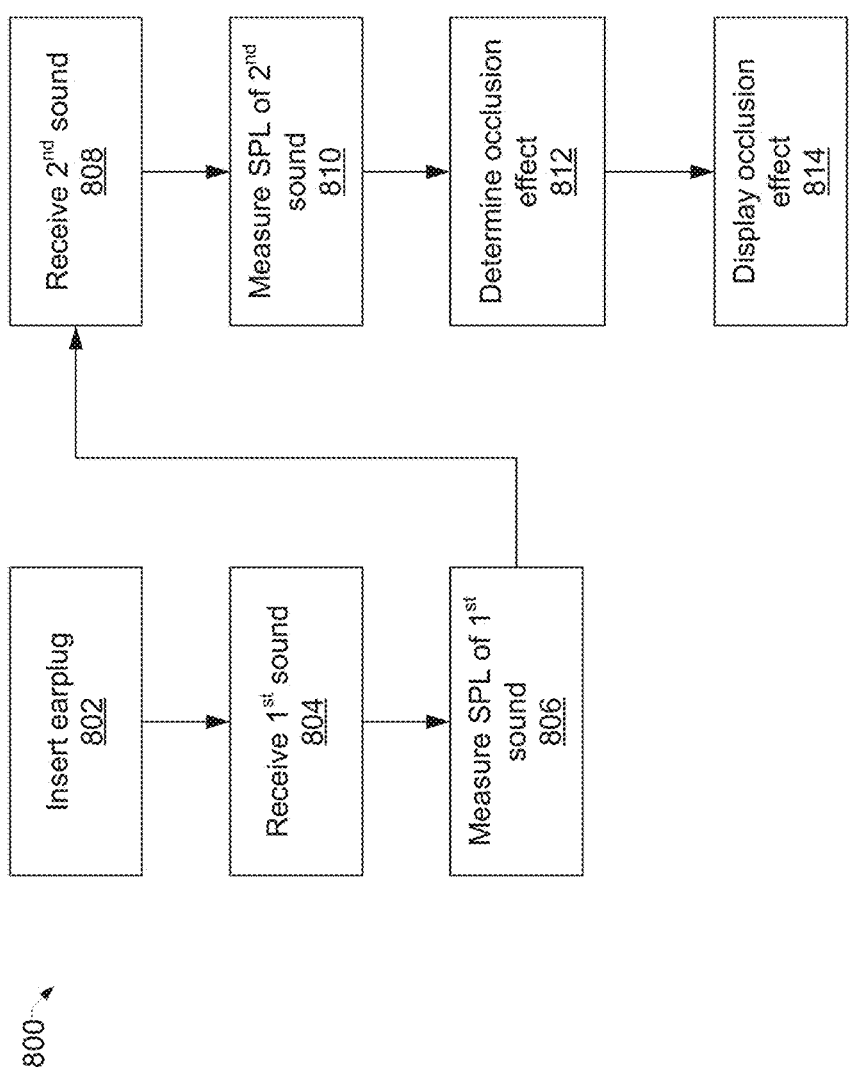
FIG. 8 is an example flow diagram for determining occlusion effect in accordance with an embodiment of the disclosure.

FIG. 8 is an example flow diagram for determining an occlusion effect in accordance with an embodiment of the disclosure. Referring to FIG. 8, there is shown a flow diagram 800. At block 802 an earpiece is inserted in to an ear of the subject for occlusion effect measurement. The earpiece may be an HPD, a hearing aid that is turned off, a measurement device, or part of a hearing protection device. In the case of an HPD or a hearing aid, a probe tube may be needed to bring sound from the ear canal to the microphone unless the HPD has a microphone open to the ear canal past the HPD as described in U.S. Pat. No. 9,198,800.

At block 804, the first sound is received due to the subject making the sound "EEE." At block 806, the SPL of the sound "EEE" is measured. Various embodiments may allow the received sound to be transmitted via wired or wireless transmission for processing.

At block 808, the second sound is received due to the subject making the sound "AHH." At block 810, the SPL of the sound "AHH" is measured. At block 812, the occlusion effect is calculated. For example, the occlusion effect can be calculated as the difference between the SPL of the sound "EEE" and the sound "AHH."

At block 814, the occlusion effect can be displayed on a display.

To provide further accuracy, various embodiments of the disclosure may have the subject repeat the two sounds one or more times. Accordingly, the blocks 804 to 812 may be repeated as needed. These embodiments may need to be able to store the sounds and/or determinations in memory. One method for more accuracy may be to average the occlusion effect measurements, however, the various embodiments of the disclosure need not be so limited and other methods for providing greater accuracy may be used.

Figure 9:
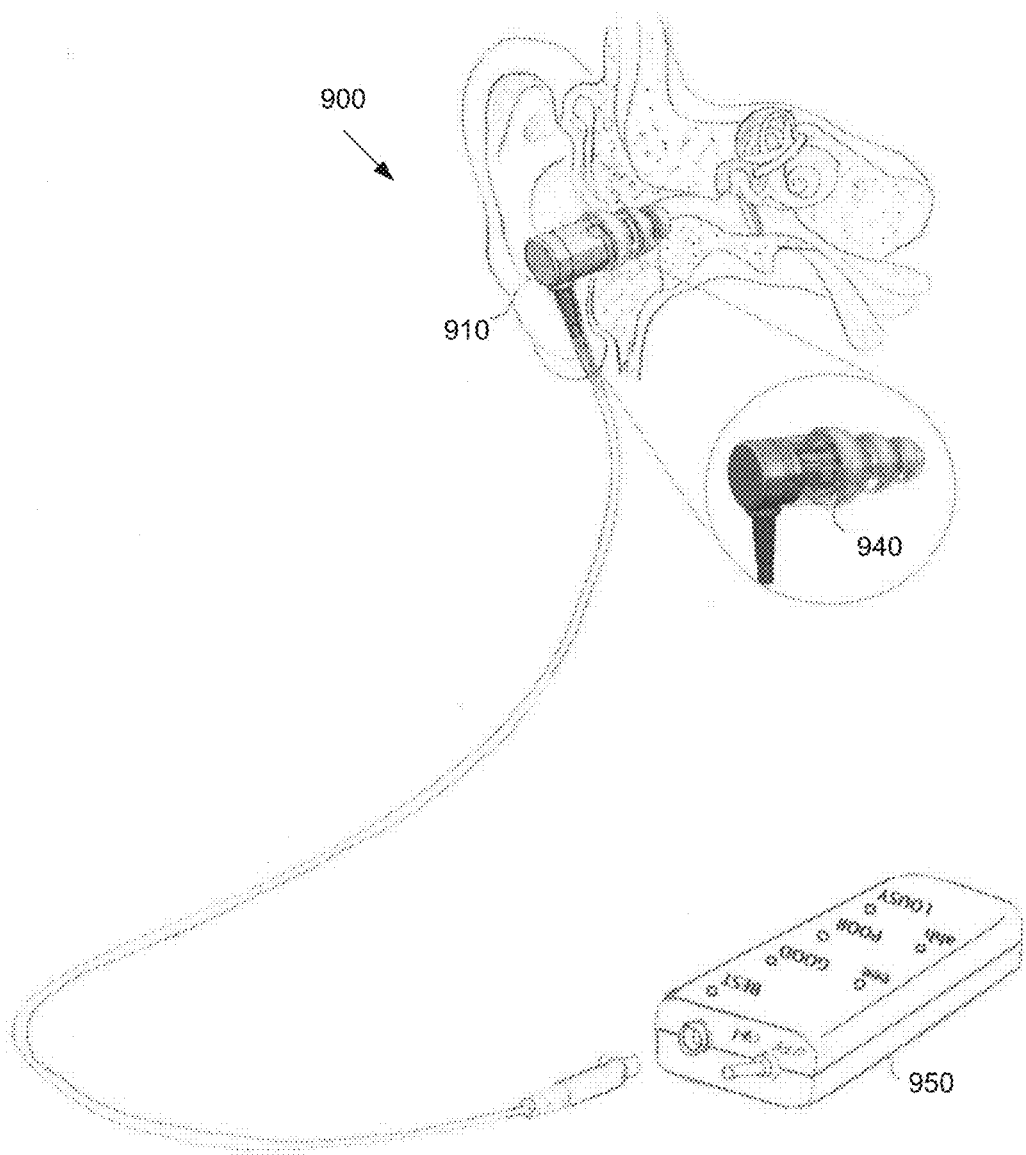
FIG. 9 is a drawing showing an example earpiece with a built-in microphone and a display device in accordance with an embodiment of the disclosure.

FIG. 9 is a drawing showing an example earpiece with a built-in microphone and a display device in accordance with an embodiment of the disclosure. Referring to FIG. 9, there is shown the communication device 900 that can be connected to, for example, the measurement device 950. The communication device 900 comprises the earpiece 910 with the built-in microphone 940. The built-in microphone 940 converts sound waves in the ear canal to electrical signals and communicates the electrical signals to the measurement device 950. The sound waves are due to the subject making specific sounds as indicated by the measurement device 950. For example, an LED may light up by the label "EEE" to indicate that the subject should make an "EEE" sound or an LED may light up by the label "AHH" to indicate that the subject should make an "AHH" sound. Some embodiments may keep the LED turned on for the duration that the subject should make the sound.

In the embodiment shown in FIG. 9, the measurement device 950 processes the electrical signals to output a simple determination of how well the earpiece 910 is fit in the ear canal of the subject. For example, if the occlusion effect is in a low range, the LED next to the label "Best" may light. If the occlusion effect is in a little higher range, the LED next to the label "Good" may light up. If the occlusion effect is in a higher range still, the LED next to the label "Poor" may light. If the occlusion effect is in the highest range, the LED next to the label "Lousy" may light up. It should be understood that this is a specific implementation of the disclosure, and various embodiment need not be limited so. For example, there may be a different number of ranges, and the labels may be different words, numbers, text, and/or figures.

The measurement device could also be used to compare the ear canal SPL for "EEE" sound when the devices is in place in the ear to the SPL outside the ear when the devices is removed from the ear and held near the ear. The memory 158, for example, can retain the required information for "EEE" and "AHH" to make the desired comparison.

Also, while the first sound was stated to be "EEE" and the second sound "AHH," it should be understood that the "AHH" could be said first and "EEE" second. Additionally, while the sounds "EEE" and "AHH" are given as examples, other sounds can be used if they are appropriate.

Accordingly, an aspect of an example embodiment provides a system that is configured to obtain sound pressure level (SPL) measurements from an ear canal to determine the occlusion effect. For many applications, the importance of the measured occlusion effect is that it provides a good estimate of the attenuation of the earplug or HPD. The system includes an earpiece (20, 150, 910) configured for insertion in the ear canal, a single microphone (40, 152, 240) configured to receive sound waves from an ear canal side of the earpiece (20, 150, 910) and transduce the sound waves into electrical signals, and a processing device (60, 70, 154, 156, and/or 162, etc.) configured to receive the electrical signals from the single microphone (40, 152, 940) and process the electrical signals into processed signals to display on a display device (95, 164, 950), wherein the processed signals are a result of only the electrical signals from the single microphone (40, 152, 940). In the case of an earpiece 910 with built-in microphone 940, which senses the sound in the ear canal, a simple occlusion effect measurement is enabled without need for a probe tube through or along the earpiece.

There is also provided a method for obtaining sound pressure level (SPL) measurements from an ear canal to determine the occlusion effect, as described by the disclosure in general, and the flow diagram of FIG. 8. The method includes an earpiece (20, 150, 910) being inserted in to a subject's ear canal (at 802), receiving a first sound stimulus (at 804) at a microphone (40, 152, 940), and determining, by a processing device (60, 70, 154, 156, and/or 162, etc.), a first SPL of the first sound stimulus from the first electrical signals received from the microphone (at 806). The method further includes receiving a second sound stimulus (at 808) at the microphone (40, 152, 940), determining, by the processing device (60, 70, 154, 156, and/or 162, etc.), a second SPL (at 810) of the second sound stimulus from second electrical signals received from the microphone (40, 152, 940). The method then includes comparing the first SPL to the second SPL to determine occlusion effect (at 812) provided by the earpiece (20, 150, 910), and presenting (at 814), at a display device (95, 164, 950), the determined occlusion effect.

Various embodiments of the disclosure may be implemented in hardware and/or software, and the software may be written as computer programs and may be implemented in general-use digital computers or specialized processors that execute the programs using a non-transitory computer-readable recording medium.

Non-transitory computer-readable recording medium may include, for example, magnetic storage media (e.g., ROM, floppy disks, hard disks, etc.), optical recording media (e.g., CD-ROMs, or DVDs), etc.

While various embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed:

1. A system configured to obtain sound pressure level (SPL) measurements from an ear canal to determine an occlusion effect, the system comprising:
    an earpiece configured for insertion in the ear canal;
    a single microphone configured to receive sound waves from an ear canal side of the earpiece and transduce the sound waves into electrical signals; and
    a processing device configured to receive the electrical signals from only the single microphone and process the electrical signals into processed signals to display on a display device.

2. The system of claim 1, wherein the processing device comprises:
    a filter configured to receive the electrical signals from the single microphone to generate a filtered output; and
    a rectifier unit configured to generate the processed signal from the filtered output.

3. The system of claim 2, wherein the display device is configured to display the processed signals in decibels.

4. The system of claim 2, wherein the rectifier unit comprises an amplifier.

5. The system of claim 4, wherein the display device is configured to display the processed signals in decibels.

6. The system of claim 2, wherein the filter is a bandpass filter with a center frequency of substantially 250 Hz.

7. The system of claim 1, wherein the processed signals correlate to the occlusion effect.

8. The system of claim 1, wherein the processed signals correlate to an attenuation of sound due to the earpiece.

9. The system of claim 1, comprising a probe tube configured to extend from the ear canal side of the earpiece to the single microphone, the probe tube configured to transmit sound waves to the single microphone.

10. The system of claim 1, wherein at least a portion of the processing the electrical signals to processed signals is performed with analog circuits.

11. The system of claim 1, wherein the system comprises a memory device to store the processed signals.

12. The system of claim 1, wherein at least a portion of processing the electrical signals to processed signals is performed digitally.

13. A method for obtaining sound pressure level (SPL) measurements from an ear canal to determine an occlusion effect, the method comprising:
    inserting an earpiece into the ear canal;
    receiving a first sound stimulus at a microphone;
    determining, by a processing device, a first SPL of the first sound stimulus from first electrical signals received from the microphone;
    receiving a second sound stimulus at the microphone;
    determining, by the processing device, a second SPL of the second sound stimulus from second electrical signals received from the microphone;
    comparing the first SPL to the second SPL to determine the occlusion effect provided by the earpiece; and
    presenting, at a display device, the determined occlusion effect.

14. The method of claim 13, wherein the first sound stimulus and the second sound stimulus are provided by a voice of a user who has the earpiece in the ear canal.

15. The method of claim 14, wherein the first sound stimulus is an "EEE" sound and the second sound stimulus is an "AHH" sound.

16. The method of claim 13, wherein the first sound stimulus and the second sound stimulus are measured in decibels.

17. The method of claim 13, wherein at least one of the first electrical signals, the second electrical signals, and the determined occlusion effect are received wirelessly by the display device.

18. The method of claim 13, wherein a difference between the second sound stimulus and the first sound stimulus are presented at the display device in decibels.

19. The method of claim 13, comprising filtering the first sound stimulus and the second sound stimulus received by the microphone with one of a low pass filter having a cutoff frequency above 250 Hz and a bandpass filter having a center frequency of substantially 250 Hz.

20. The method of claim 13, wherein a probe tube is configured to extend from an ear canal side of the earpiece to the microphone, and the probe tube is configured to transmit the first sound stimulus and the second sound stimulus to the microphone.

21. The method of claim 13, wherein the first sound stimulus and the second sound stimulus are provided multiple times for use in determining the occlusion effect.

22. The method of claim 13, comprising storing in memory the first sound stimulus and the second sound stimulus.

23. The method of claim 13, comprising estimating a sound attenuation due to the earpiece from the determined occlusion effect.

* * * * *